United States Patent [19]

Gilbert

[11] Patent Number: 4,851,593

[45] Date of Patent: Jul. 25, 1989

[54] DIHYDROXY OR POLYHYDROXY COMPOUNDS AND PROCESS FOR PRODUCING SAME

[75] Inventor: Robert M. Gilbert, Columbus, Ohio

[73] Assignee: Sherex Chemical Company, Dublin, Ohio

[21] Appl. No.: 107,310

[22] Filed: Oct. 13, 1987

[51] Int. Cl.$^4$ ..................... C07C 29/136; C07C 27/04
[52] U.S. Cl. ..................................... 568/864; 568/852; 568/861
[58] Field of Search ................. 568/864, 821, 852, 861

[56] References Cited

U.S. PATENT DOCUMENTS

| | | | |
|---|---|---|---|
| 2,094,611 | 10/1937 | Lazier | 568/864 |
| 2,347,562 | 4/1944 | Johnston | 260/617 |
| 2,862,979 | 12/1958 | Cull et al. | 260/638 |
| 2,863,928 | 12/1958 | Indest | 568/864 |
| 2,908,721 | 10/1959 | Cull et al. | 260/638 |
| 3,215,782 | 11/1965 | Steward, Jr. et al. | 260/67 |
| 3,272,873 | 9/1966 | Porter, Jr. et al. | 260/638 |
| 3,655,791 | 4/1972 | De Young | 260/666 B |
| 3,773,842 | 11/1973 | Schirmann et al. | 260/635 A |
| 3,846,550 | 11/1974 | Akrongold et al. | 424/63 |
| 3,975,451 | 8/1976 | Fujita et al. | 260/635 Y |
| 4,181,707 | 1/1980 | Strope | 423/386 |
| 4,214,106 | 7/1980 | Freudenberger et al. | 568/864 |
| 4,482,764 | 11/1984 | Herrmann et al. | 568/864 |
| 4,483,798 | 11/1984 | Disteldorf et al. | 260/239 A |
| 4,518,810 | 5/1985 | Matsuda et al. | 568/905 |
| 4,613,707 | 9/1986 | Kouba et al. | 568/864 |
| 4,724,100 | 2/1988 | Gilbert et al. | 260/410.9 N |

FOREIGN PATENT DOCUMENTS

| | | |
|---|---|---|
| 618583 | 12/1982 | Belgium . |
| 1540611 | 8/1968 | France . |
| 6405131 | 12/1964 | Netherlands . |
| 6511426 | 3/1966 | Netherlands . |
| 1001467 | 8/1965 | United Kingdom . |
| 1015078 | 12/1965 | United Kingdom . |
| 1043507 | 9/1966 | United Kingdom . |
| 1132033 | 10/1968 | United Kingdom . |
| 1462228 | 1/1977 | United Kingdom . |

*Primary Examiner*—Werren B. Lone
*Attorney, Agent, or Firm*—Pollock, Vande Sande & Priddy

[57] ABSTRACT

Dihydroxy and polyhydroxy compounds are obtained from polymerized fatty acids by a liquid phase reaction at a temperature at about 500° F. to about 650° F., pressures up to about 1000 psi in the presence of a catalytic amount of a hydrogenation catalyst, along with removal of water by-product during the reaction.

23 Claims, No Drawings

DIHYDROXY OR POLYHYDROXY COMPOUNDS AND PROCESS FOR PRODUCING SAME

TECHNICAL FIELD

The present invention is concerned with certain dihydroxy and polyhydroxy compounds and to a process for producing the dihydroxy and polyhydroxy compounds from the corresponding polymerized fatty acids.

In particular, the present invention is concerned with a liquid phase hydrogenation process for preparing dihydroxy and polyhydroxy compounds that require relatively moderate pressures and to compounds obtained by the process.

The dihydroxy and polyhydroxy compounds obtained pursuant to the present invention are especially suitable as reactants with polyisocyanates in producing polyurethanes.

BACKGROUND ART

Diols and polyols derived from polymerized fatty acids, i.e., dimerized and oligomerized fatty acids have been suggested.

Processes for obtaining such diols and polyols have been suggested whereby the lower alkyl esters of the fatty acids have been dimerized followed by hydrogenating under relatively high pressure or by dimerizing the fatty acid and then converting the dimerized fatty acid to the lower alkyl ester and then hydrogenating under relatively high pressure.

In view of the fact that use of the lower alkyl ester was a relatively uneconomical pressure in view of the additional costs involved with the esterification stage and subsequent removal of alcohol, direct hydrogenation of dimerized fatty acids that contain free carboxyl groups has been attempted. However, dimerized fatty acids that contain two free carboxyl groups are difficult to hydrogenate.

For instance, the catalysts employed were relatively sensitive to the free acids and to the water of reaction that occurs during the hydrogenation of the acids. Moreover, the presence of the free carboxylic acids has a tendency to attack the equipment, particularly under conditions whereby high pressures and high temperatures are required. This, in turn, has led to use of equipment that requires special corrosion-resistant materials.

In view of the various problems encountered, a high-pressure process whereby the polymerized fatty acid starting material is continually introduced into the reaction medium, i.e., a suspension in an amount that during the hydrogenation the amount of polymerized fatty acid present does not exceed the weight of the desired product present as discussed in British Pat. No. 1,132,033.

Although such process overcomes a number of the concerns and problems previously encountered, such process still requires relatively severe pressures and temperatures that it is necessary to employ high pressure equipment. Furthermore, the process suggested therein requires careful monitoring so that the added acid is maintained within the required limits.

SUMMARY OF INVENTION

The present invention is concerned with a process for preparing dihydroxy and polyhydroxy compounds by catalytic hydrogenation of polymerized fatty acids under relatively moderate pressure conditions.

Accordingly, the process of the present invention eliminates the need for relatively expensive high-pressure equipment. In addition, the process of the present invention does not tend to cause stress cracking, and corrosion of the equipment as experienced when employing high pressure (e.g. - about 3000 psi to 4000 psi) hydrogenation techniques. Furthermore, in carrying out the present invention, normal line pressures are adequate for the hydrogen; whereas, in high pressure processes (e.g. - 1500 psi and above), a high pressure tank is required for the hydrogen storage.

In particular, the present invention is concerned with a liquid phase process that comprises subjecting the polymerized fatty acid in a reaction zone under a hydrogen atmosphere to a temperature of about 500° F. to about 650° F. at a pressure of about 400 psi to about 600 psi. The reaction is carried out in the presence of a catalytic amount of a hydrogenation catalyst. In addition, water by-product of reaction is removed from the reaction zone during the hydrogenation of the polymerized fatty acid to the desired dihydroxy or polyhydroxy compound.

The products obtained by the present invention have hydroxyl values of at least about 50, acid value of about 4 or less, and ester value of about 20 to about 75.

BEST AND VARIOUS MODES FOR CARRYING OUT INVENTION

The polymerized fatty acids employed as the starting materials in the process of the present invention can be obtained from unsaturated or saturated fatty acids or their corresponding lower alkyl esters by dimerization or oligomerization.

Examples of such fatty acids that can be dimerized or oligomerized include palmitoleic acid, oleic acid, elaidic acid, erucic acid, linoleic acid, and linolenic acid.

The polymerized fatty acids include saturated, as well as unsaturated fatty acids in the product. Mixtures of the various acids can be employed when desired. The term "polymerized fatty acid" comprises the pure dicarboxylic dimeric acids that are obtained by distillation, dicarboxylic co-dimeric acids, and polycarboxylic co-oligomeric acids, and mixtures of there with amounts of monocarboxylic, monomeric, tricarboxylic trimeric, and/or polycarboxylic oligomeric acids.

In the same way, the dihydroxy and polyhydroxy compounds obtained are products of the hydrogenation, are dimeric or oligomeric alcohols, or corresponding mixtures.

The polymerized fatty acids usually contain about 32 to about 54 carbon atoms and preferably about 36 to about 40 carbon atoms. The predominate portion of the polymerized fatty acids can be saturated or unsaturated, depending upon the desired products.

The process of the present invention is carried out under a hydrogen atmosphere to effect dehydrogenation of the polymerized fatty acid at a temperature of about 500° F. to about 650° F., preferably at about 500° F. to about 600° F., and most preferably at about 550° F. to about 590° F.

The pressure employed is up to about 1000 psi, preferably up to about 600 psi, and most preferably about 400 psi to about 600 psi.

The reaction is generally completed in about 2 hours to about 20 hours and most usually in about 3 hours to about 7 hours.

In addition, the process of the present invention is carried out in the presence of a catalytic amount of a hydrogenation catalyst. Suitable hydrogenation catalysts include copper and cadmium, or copper and zinc, or copper and chromium which may be in the form of the hydroxide and/or carbonate.

When it is desired to maintain unsaturation that may be present in the acid, the cadmium can serve to protect the unsaturated groups from being hydrogenated. When the process of the present invention is concerned with obtaining saturated dihydroxy or polyhydroxy compounds, zinc in the form of, for instance, zinc hydroxide or zinc acetate, can be employed instead of the cadmium.

Other catalysts known to effect hydrogenation can be employed in accordance with the present invention. Examples of such include copper chromite and zinc chromate.

The catalyst is generally employed in amounts of about 1% to about 5% by weight of total metals based upon the acid feed and preferably about 2% by weight of total metals based upon the acid feed.

Typical copper-cadmium or zinc catalysts contain about 4 parts by weight of copper to about 1 part by weight of cadmium or zinc to about 1 part by weight of copper to about 4 parts by weight of cadmium or zinc, and preferably about 2 parts by weight of copper to about 1 part by weight of cadmium or zinc.

In accordance with the present invention, it is essential that at least about 50% of the water byproduct of reaction be removed during the process in order to achieve the high yields of dihydroxy and polyhydroxy compounds under the moderate pressure conditions employed. However, not all of the water byproduct is removed since a small portion of the total should remain in order to facilitate continuance of the reaction. For instance, about 25% to about 50% of the total water by-product formed is usually not removed during the process. The specific amount of water to remain can be readily determined by persons skilled in the art without undue experimentation once aware of the present disclosure. The water can be removed by employing a sparge technique using a gas such as hydrogen. The sparge technique is preferably carried out by continuous sparging of the reaction mixture. The sparge rate must be sufficient to prevent significant build-up of water. In a typical reaction containing about 500 grams to about 1,000 grams of the polymerized fatty acid, the sparge rate is usually at least about 0.5 standard cubic feet per hour of hydrogen and preferably about 0.5 standard cubic feet per hour to about 10 standard cubic feet per hour of gas and most preferably about 1 standard cubic foot per hour for a reaction vessel such as a two-liter pressure vessel containing about 500 grams to about 1,000 grams of polymerized fatty acid.

Another method for removing water during the reaction is a periodic venting procedure whereby periodically the reactor is vented to reduce the pressure, followed by repressurizing to the desired pressure at stated intervals. One particular venting procedure involves reducing the pressure by venting approximately every thirty minutes of the reaction period. The pressure during the venting is reduced at least by about 100 psi and preferably by about 200 psi toabout 300 psi. After the venting by the reduction pressure, the reaction vessel is repressurized with hydrogen to the desired pressure such as at about 400 psi to about 600 psi.

The process of the present invention usually provides yields which are essentially quanitative (e.g. - at least about 95%). The dihydroxy and polyhyroxy compounds obtained in accordance with the present invention have a minimum hydroxyl number of about 50, acid values of about 4 or lower, and an ester value of at least about 20. More usually, the products obtained by the process of the present invention exhibit a hydroxyl number of about 50 to about 135, acid value or less than 1 to about 4, and an ester value of about 20 to about 75, and preferably about 35 to about 75. The preferred hydroxyl number is about 70 to about 135.

The dihydroxy and polyhydroxy products obtained in accordance with the present invention are especially useful in the preparation of polyurethanes.

The following non-limiting examples are presented to further illustrate the present invention. All of the following examples use about 350 grams of the polymerized fatty acid.

EXAMPLE 1

Into a two-liter pressure reactor fitted with stirrer and heatingcooling coils are introduced about 350 grams of a dimerized fatty acid having an acid value of about 190 to 198, a saponification value of about 194 to 200, containing about 87% by weight of C-36 dimer dicarboxylic acid, and about 13% by weight of C-54 trimer tricarboxylic acid available from Emery under the trade designation Empol-1016, about 21 grams of $Cu(OH)_2$, and about 14 grams of copper chromite.

A vacuum of about 30 mm is applied in order to remove air from the reaction vessel. After this, hydrogen is introduced into the reaction vessel in order to increase the pressure to about 600 psi. The reaction mass is then brought to a temperature of about 560° F. A sparge employing hydrogen gas at about 1 standard cubic foot per minute is applied to the reaction mass to remove water formed from the reaction. The reaction mass is maintained under these conditions for about 4 hours. After this, the reaction mass is cooled to about room temperature and the catalyst is removed from the product by filtration.

The product has a hydroxyl value of about 89.4, an acid value of about 0.4, a saponification value of about 21, and an iodine value of about 20. The yield is about 95% of the acid feed.

EXAMPLE 2

Into a two-liter pressure reactor fitted with stirrer and heating-cooling coils are introduced about 350 grams of polymerized fatty acid available under the trade designation Empol-1016, about 10.5 grams of $Cu(OH)_2$, and about 7 grams of copper chromite.

A vacuum of about 30 mm is applied in order to remove air from the reaction vessel. After this, hydrogen is introduced into the reaction vessel in order to increase the pressure to about 600 psi. The reaction mass is then brought to a temperature of about 550° F. A sparge employing hydrogen gas of about 1 standard cubic foot per minute is applied to the reaction mass to remove water by-product formed from the reaction. The reaction mass is maintained under these conditions for about 6 hours. After this, the reaction mass is cooled to about room temperature and the catalyst is then removed from the product by filtration.

The product has a hydroxyl value of about 72.6, an acid value of about 3.3, a saponification value of about 66.2, and an iodine value of about 82.2. The yield is about 95% of the feed carboxylic acid.

EXAMPLE 3

Into a two-liter pressure reactor fitted with stirrer and heating-cooling coils are introduce about 350 grams of polymerized fatty acid available under the trade designation Empol-1016, about 4.69 grams of Cu(OH)$_2$, and about 2.31 grams of Cd(OH)$_2$.

A vacuum of about 30 mm is applied in order to remove air from the reaction vessel. After this, hdyrogen is introduced into the reaction vessel in order to increase the pressure to about 600 psi. The reaction mass is then brought to a temperature of about 570° F. A sparge employing hydrogen gas of about 1 standard cubic foot per minute is applied to the reaction mass to remove water formed from the reaction. The reaction mass is maintained under these conditions for about 3 hours. After this, the reaction mass is cooled to about room temperature and the catalyst is then removed from the reaction product by filtration.

The product obtained has a hydroxyl value of about 126, an acid value of about 4, and a saponification value of about 48.2. The yeild of product is about 95% of the acid feed.

Having thus described our invention, what we claim as new and desire to secure by Letters Patent is:

1. A liquid phase process for preparing dihydroxy or polyhydroxy compound by catalytic hydrogenation of polymerized fatty acid which comprises:

subjecting said polymerized fatty acid in a reaction zone under a hydrogen atmosphere to a temperature of about 500° F. to about 650° F. at a pressure up to about 600 psi in the presence of a catalytic amount of a hydrogenation catalyst and removing water product of reaction from the reaction zone during the hydrogenation of the polymerized fatty acid and thereby obtaining said dihydroxy or polyhydroxy compound.

2. The process of claim 1 wherein said polymerized fatty acid is an unsaturated acid.

3. The process of claim 1 wherein said fatty acid is a saturated acid.

4. The process of claim 1 wherein said acid includes dimerized fatty acid.

5. The process of claim 1 wherein said acid includes trimerized fatty acid.

6. The process of claim 1 wherein said polymerized fatty acid contains about 32 carbon atoms to about 54 carbon atoms.

7. The process of claim 1 wherein said polymerized fatty acid contains about 36 to about 40 carbon atoms.

8. The process of claim 1 wherein said temperature is about 500° F. to about 650° F.

9. The process of claim 1 wherein said temperature is about 500° F. to about 650° F.

10. The process of claim 1 wherein said temperature is about 550° F. to about 590° F.

11. The process of claim 1 wherein said pressure is about 400 psi to about 600 psi.

12. The process of claim 1 wherein said catalyst contains a source of copper.

13. The process of claim 1 wherein said catalyst contains a source of copper and cadmium.

14. The process of claim 1 wherein said catalyst comprises a source of copper and zinc.

15. The process of claim 1 wherein said catalyst comprises a source of copper and cadmium.

16. The process of claim 1 wherein the water is removed by venting the reaction vessel in order to reduce the pressure by at least about 100 psi.

17. The process of claim 1 wherein the water is removed by venting the reaction vessel in order to reduce the pressure by at least about 200 psi.

18. The process of claim 17 wherein the pressure is reduced intermittently and repressurized approximately every 30 minutes of the reaction.

19. The process of claim 1 wherein the yield is at least about 95%.

20. The process of claim 1 wherein said dihydroxy or polyhydroxy compound has a hydroxyl value of at least about 50, an acid value of 4 or less, and a saponification value of about 20 to about 75.

21. Dihydroxy or polyhydroxy compound having a hydroxyl value of at least about 50, an acid value of 4 or less, an ester value of about 20 to about 75, and obtained by the process of claim 1.

22. The process of claim 1 wherein at least about 50% and less than the total of the water product of reaction is removed from the reaction zone during said hydrogenation.

23. The process of claim 22 wherein said about 25% to about 50% of the total water product of reaction is not removed from the reaction zone during said hydrogenation.

* * * * *